US006623422B2

(12) United States Patent
Kamrava

(10) Patent No.: US 6,623,422 B2
(45) Date of Patent: Sep. 23, 2003

(54) METHOD AND APPARATUS FOR ASSISTED EMBRYO IMPLANTATION

(75) Inventor: Michael Kamrava, Los Angeles, CA (US)

(73) Assignee: Napoli, LLC, Beverly Hills, CA (US)

( * ) Notice: Subject to any disclaimer, the term of this patent is extended or adjusted under 35 U.S.C. 154(b) by 224 days.

(21) Appl. No.: 09/759,415

(22) Filed: Jan. 12, 2001

(65) Prior Publication Data

US 2002/0095065 A1 Jul. 18, 2002

(51) Int. Cl.[7] .................................................. A61B 17/43
(52) U.S. Cl. ............................ 600/34; 600/33; 600/35; 600/34; 128/898
(58) Field of Search ........................... 600/33, 34, 35; 604/264; 128/898

(56) References Cited

U.S. PATENT DOCUMENTS

| 4,203,430 A |   | 5/1980  | Takahashi       |         |
|-------------|---|---------|-----------------|---------|
| 4,534,339 A |   | 8/1985  | Collins et al.  |         |
| 4,779,612 A |   | 10/1988 | Kishi           |         |
| 4,846,785 A | * | 7/1989  | Cassou et al.   | 600/34  |
| 4,911,148 A |   | 3/1990  | Sosnowski et al.|         |
| 5,195,979 A |   | 3/1993  | Schinkel et al. |         |
| 5,217,466 A |   | 6/1993  | Hasson          |         |
| 5,360,389 A | * | 11/1994 | Chenette        | 600/34  |
| 5,472,419 A | * | 12/1995 | Bacich          | 604/55  |
| 5,484,422 A |   | 1/1996  | Sloane, Jr. et al.|       |
| 5,656,010 A | * | 8/1997  | Li et al.       | 600/34  |
| 5,772,628 A |   | 6/1998  | Bacich et al.   |         |
| 5,843,023 A | * | 12/1998 | Cecchi          | 604/44  |
| 5,961,444 A | * | 10/1999 | Thompson        | 600/33  |
| 6,004,302 A |   | 12/1999 | Brierley        |         |
| 6,006,002 A |   | 12/1999 | Motoki et al.   |         |
| 6,010,448 A | * | 1/2000  | Thompson        | 600/34  |
| 6,027,443 A |   | 2/2000  | Nag             |         |
| 6,053,899 A |   | 4/2000  | Slanda et al.   |         |
| 6,156,566 A | * | 12/2000 | Bryant          | 435/305.3 |
| 6,203,533 B1|   | 3/2001  | Ouchi           |         |
| 6,258,070 B1| * | 7/2001  | Kaldany         | 604/264 |
| 6,273,877 B1| * | 8/2001  | West et al.     | 604/264 |
| 6,280,423 B1| * | 8/2001  | Davey et al.    | 604/264 |
| 6,281,013 B1| * | 8/2001  | Grondahl        | 435/363 |
| 6,319,192 B1| * | 11/2001 | Engel et al.    | 600/33  |

FOREIGN PATENT DOCUMENTS

| DE | 3702441 A1   | 1/1987 |
| GB | 2118840 A    | 3/1983 |
| WO | WO 97/13451  | 4/1997 |

OTHER PUBLICATIONS

Itskovitz–Eldor et al., *Assisted implantation: direct intraendometrial embryo transfer,* Gynecologic & Obstetric Investigation, vol. 43, No. 2 pp. 73–5, 1997.

Wang, Huaixiu, et al., *Decreased in vitro fertilization and cleveage rates after an equipment error during $CO_2$ calibration,* Fertility and Sterility, vol. 73, No. 6 pp. 1247–1249, Jun. 2000.

Lesny, Piotr et al., *Transcervical embryo transfer as a risk factor for ectopic pregnancy,* Fertility and Sterility, vol. 72, No. 2 pp. 305–309, Aug. 1999.

Goto, Noda, Y., et al., *Pregnancy achieved by transferring blastocysts into endometrial stroma in mice,* Human Reproduction, vol. 7, No. 5 pp. 681–4, May 1992 Abstract Only.

(List continued on next page.)

*Primary Examiner*—Denise L. Esquivel
*Assistant Examiner*—Tu Cam Nguyen
(74) *Attorney, Agent, or Firm*—Blakely Sokoloff Taylor & Zafman LLP

(57) ABSTRACT

A method and apparatus for assisted embryo implantation using a specialized microcatheter to prepare an implantation site within the subject's endometrial lining and to transport and place an embryo into the implantation site.

21 Claims, 4 Drawing Sheets

OTHER PUBLICATIONS

Balmaceda JP, et al., Hysteroscopy and assisted reproductive technology, *Obstet Gynecol Clin North Am* vol. 22, No. 3, pp. 507–18, Sep. 1995 Abstract Only.

Asaad M., et al., *"Twin pregnancy following transmyometrial–subendometrial embryo transfer for repeated implantation failure,"* Human Reproduction, vol. 12, No. 12, pp. 2824–5, 1997, Abstract Only.

Brunk, D., "Blastocyst Transfer Cuts Multiples Risk," Ob.Gyn.News vol. 35, No. 23.

"Flexible Hysteroscopes," Contemporary OB/GYN, Apr. 15, 1999, Medical Economics, Montvale, NJ, pp. 6–11.

* cited by examiner

METHOD AND APPARATUS FOR ASSISTED EMBRYO IMPLANTATION

BACKGROUND OF THE INVENTION

1. Field of the Invention

The present invention relates to the field of embryo implantation into the endometrial lining of the uterus of an in-vitro fertilized (IVF) embryo. More particularly to an implantation method using a novel microcatheter, with a shaped tip, capable of both forming a pocket in the uterine wall and transferring an embryo into the pocket. To aid the movement of the microcatheter to the implantation site, a hybrid endoscope insertion arm has been developed with a flexible free end extending seamlessly from a rigid base section.

2. Description of the Related Arts

Improving the success of IVF depends on many factors, one of which is the delivery or transfer of the embryo to the endometrial lining of the uterus and the successful implantation of the embryo therein. It is well known in the art that assisting an embryo to adhere to, or implant within, a pre-determined area of the endometrial lining of the uterine wall, as opposed to simply releasing the embryo into the uterus, will enhance the success of IVF.

One method of assisted embryo transfer is found in U.S. Pat. No. 6,010,448 to Thompson in which an embryo is transferred with the aid of an endoscopic device, via a flexible catheter, to the endometrial lining and affixed thereto with an adhesive.

Another method of embryo transfer is taught in U.S. Pat. No. 5,360,389 to Chenette in which, after using pressurized $CO_2$ gas to distend the uterine walls, an endoscope is used to select an implantation site. A catheter is then used to forcibly inject the embryos into the endometrial lining.

While the embryo transfer methods of these prior art types may be generally satisfactory for their intended purposes, implantation problems can arise in which the trauma to the delicate embryos by either an injection or "adhesion" may yield less than optimal solutions and fail to achieve high IVF success rates. Accordingly, a minimally invasive embryo transfer method, which uses a specially formed microcatheter to gently deliver one or more selected embryos into a pocket formed within the endometrial lining would be desirable.

SUMMARY OF THE INVENTION

It is an object of this invention to provide a simple gentle method for embryo transfer and implantation. To accomplish this gentle transfer, an improved microcatheter with an angled tip has been developed. This microcatheter is able to work as both a microsurgical instrument, used to form an embryo-receiving pocket within the endometrial lining, and as the vehicle for transferring an embryo into the pocket. It has been observed that by gently securing an embryo within a pocket of endometrial lining, many of the risks of IVF, such as a tubal pregnancy, misplacement of the embryo, and loss of the embryo can be minimized.

Another benefit of actively implanting the embryo within the endometrial lining is derived from the fact that older embryos are used, thus providing for a longer period of observation which allows the most viable embryos to be selected. Higher accuracy in selecting the most viable older embryos yield the additional benefit that fewer embryos need to be implanted to assure a viable pregnancy, thereby minimizing the risk of high-order multiple births associated with those common IVF methods which place larger quantities of less mature embryos within the uterus. See, article by Doug Brunk in Ob.Gyn.News (Volume 35, number 23 at page 1–3) entitled: "Blastocyst Transfer Cuts Multiples Risk".

The within method preferably uses direct visualization of the implantation procedure through an endoscopic device. To enhance the field of vision of the endoscope and to increase the maneuverability of the endoscope within the uterus, the uterine walls may be distended by pressurizing the uterus with an inert, harmless gas such as $N_2$ gas. Other gases may also work, however, the use of pure $CO_2$ gas is contraindicated because of toxicity. Gynecologic & Obstetric Investigation, Volume 43 (2) at pages 73–5, 1997, entitled: "Assisted implantation: direct intraendometrial embryo transfer." This article explains that the introduction of $CO_2$ gas into the uterus to distend the uterine wall and improve endoscopic viewing, (such as that claimed in U.S. Pat. No. 5,360,389), also raises the risk of acidifying the endometrial lining and therefore reduces the viability of the implanted embryo. Moreover, mixtures of $CO_2$ and atmospheric air are not safe because of concern over fatal air embolism.

To enhance the positioning of the microcatheter at the implantation site, a hysteroscope, which is an endoscopic device for intrauterine use, is used. The endoscope both provides direct visualization within the uterus and acts as a guide and support for the microcatheter.

DETAILED DESCRIPTION OF THE PREFERRED EMBODIMENTS OF THE INVENTION

Figure 1A:
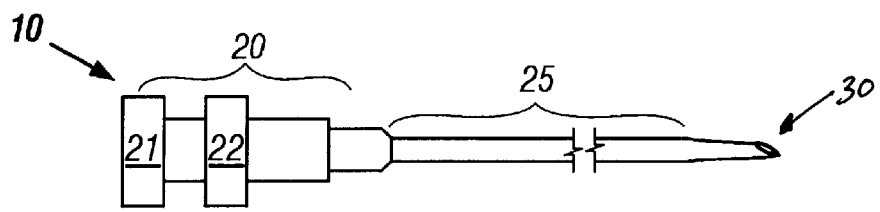
FIG. 1A is a side view of the microcatheter of the preferred embodiment.
Figure 1B:
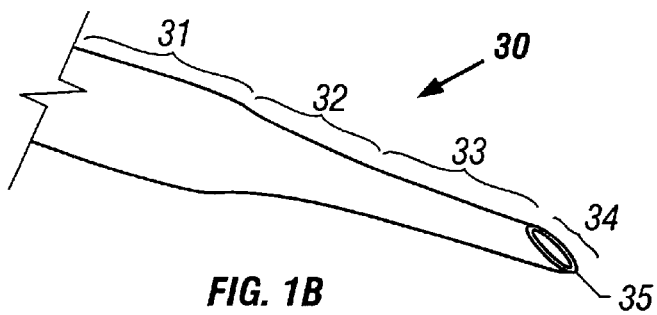
FIG. 1B is a perspective front view of the tip of the microcatheter of the preferred embodiment.
Figure 1C:
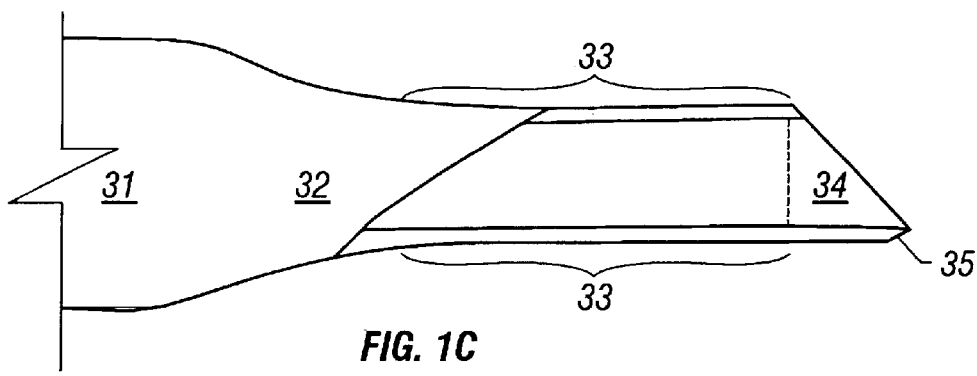
FIG. 1C is a partial cut-away side view of the tip of the microcatheter of the preferred embodiment.

Referring now to the drawings, illustrated in FIGS. 1A–1C is the preferred embodiment of a specialized microcatheter 10 having an operational syringe 20, with a plunger 21, connected to the back end 22 of a flexible hollow shaft 25 which terminates to form a shaped end 30.

The method of this invention is a minimally invasive embryo implantation into the endometrial lining of the uterus (FIG. 3). The microcatheter 10 functions both as the surgical instrument used to form the embryo-receiving pocket in the endometrial lining (FIG. 3) and as a vessel from which the embryo(s) will be transferred into the embryo-receiving pocket.

Figure 2A:
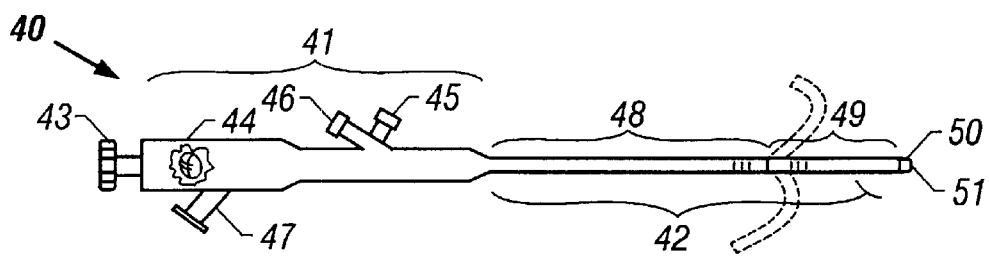
FIG. 2A is a side view of the preferred embodiment of the microcatheter of FIG. 1 supported within an endoscope.
Figure 2B:
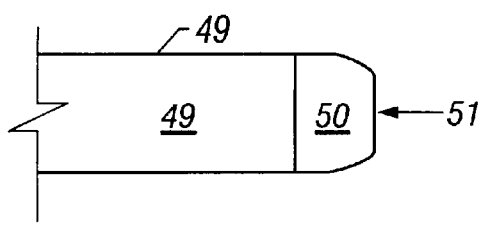
FIG. 2B is a side view of the distal end of the endoscope of FIG. 2A.
Figure 2C:
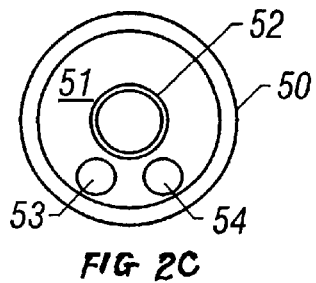
FIG. 2C is a front view of the guide face of the endoscope of FIG. 2A.

Prior to embryo implantation, an optimal implantation site is selected with the aid of an endoscopic device. The same endoscopic device may also be used as a support and guide for the microcatheter 10 as shown in FIGS. 2A, 2B and 2C. Endoscopic devices are well known in the art and it is a subcategory thereof designed for intrauterine use, known as a hysteroscope, which is preferred herein. However, acceptable results may be achieved with other similar endoscopic devices.

The hysteroscope 40 of the preferred embodiment is: Reorder #: "Special—Kamrava", manufactured to applicant's specifications by "5 Star Medical, Inc.," of Hayward, Calif. This hysteroscope 40 is a two-part elongated tubular device, with an operational section 41 at one end and an insertion section 42 at the other end. Supported on the operational section 41 is an eyepiece 43 used to visualize the uterus, a control knob 44 used to maneuver the insertion section 42, and a series of access ports 45–47 traveling from the control section 41 along both the rigid 48 and the flexible sections 49 which form the insertion section 42. The access ports 45–47 exit or terminate at the distal end 50 of the hysteroscope 40 through the guide face 51.

The basic structure of endoscopes are well known in the art, including the mechanisms for flexing the insertion section. (See, generally, U.S. Pat. No. 6,006,002 to Motoki, et al. and U.S. Pat. No. 4,534,339 to Collins, et al.) Accordingly, neither a detailed description of the endoscope structure nor the operational structure is provided. However, prior art endoscopes with wholly rigid insertion sections are unworkable with this method. The within method has been accomplished using a commercially available endoscope with a wholly flexible insertion section such as that found in a Karl Storz, Flexible Hysteroscope 3 mm diameter, manufactured by Storz of Culver City, Calif. However, a hysteroscope with a hybrid insertion section 42 having a rigid tubular base portion 48, preferably constructed of a smooth material such as stainless steel, seamlessly grafted to a flexible tubular plastic-like free end 49 has also been used to accomplish the preferred method with the additional benefits of being more easily maneuvered within the uterus and providing a responsive stable platform from which to perform the microsurgery and embryo implantation.

The gas port 45 on the operational section 41 feeds into the operational port 46 and out through the operational aperture 54. Should insufflation of the uterus be required an inert gas, such as $N_2$ 101, may be directed into the uterus through the operational aperture 52 by attaching a gas line (not shown) to the gas port 45. Illumination within the subject's uterus "U" is added via the light aperture 53 which is connected to the light port 47. Not shown is the light-producing element which mates with the light port 47. To provide for direct visualization within the subject's uterus, an eyepiece 43 is connected via an internal fiber optic (not shown) to the optical aperture 54. To perform the embryo implantation (FIG. 3) a microcatheter is inserted into the operational port 46 and its shaped end 30 extends from the guide face 51 through the operational aperture 52.

The shaped end 30 of the microcatheter 10 (FIGS. 1B and 1C) is a multi-function device. The base region 31 of the shaped end 30 is of a similar diameter as the flexible hollow shaft 25 and then tapers 32 over 1–3 millimeters into a narrower front end 33 which is ideally between 10 and 15 millimeters in length, with a diameter of 0.8 millimeters. The front end 33 terminates at an angle between 10 and 15 degrees to form an angled tip 34. The angled tip 34 is the vehicle through which the embryo is delivered into the implantation site and is also the microsurgical instrument (FIG. 3) used to form the implantation pocket (FIG. 3B) within the endometrial lining. A beveled or tapered edge 35 may be added to the angled tip 34 to yield a more refined cutting tool.

FIGS. 3B–3E show the sequential performance of the embryo implantation procedure using the preferred method of this invention. The biology, timing and biochemistry involved in embryo selection and in optimizing the subject for implantation is not the topic of this invention. It is well known by those skilled in the art of how best to harvest and fertilize eggs and how best to select viable embryos. Volumes of scientific literature also exists on the hormonal, pharmaceutical and other chemical factors which should be orchestrated, monitored and taken into account when selecting the timing for embryo implantation. Accordingly, such information is omitted.

Figure 3A:
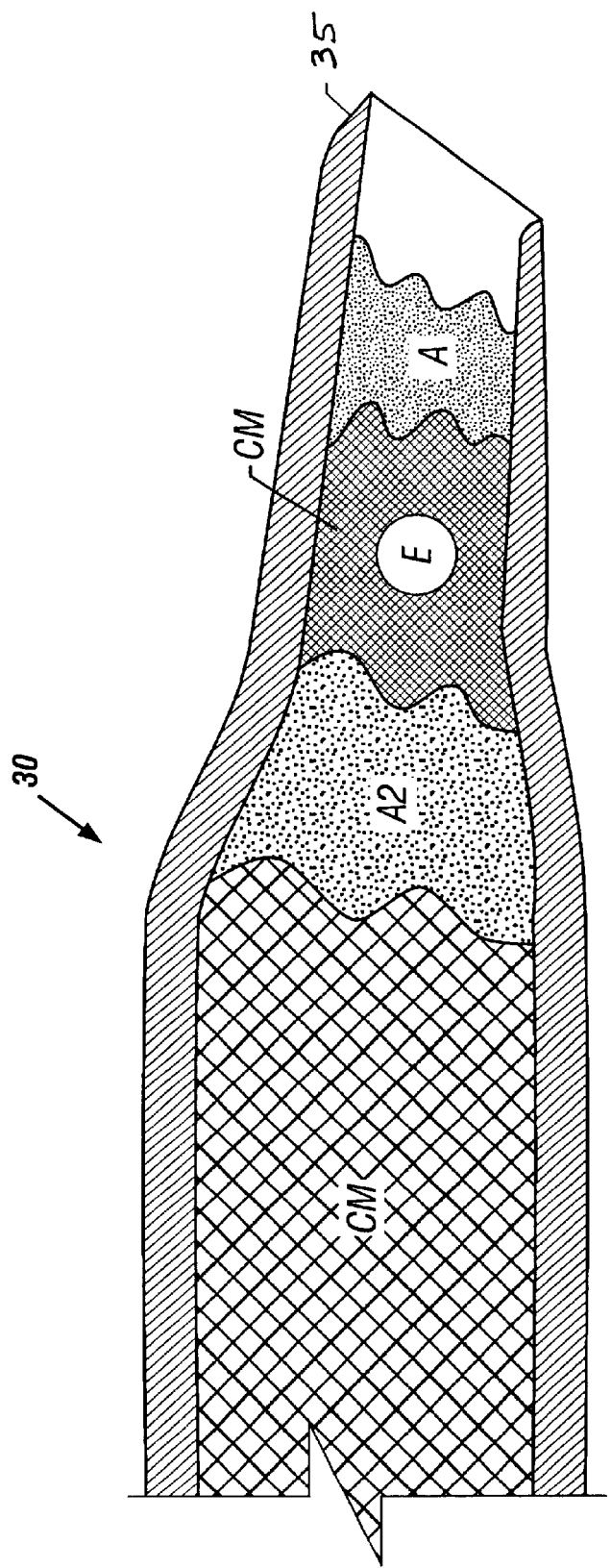
FIG. 3A is a cut-away side view of the end of the microcatheter containing an embryo for implantation.
Figure 3B:
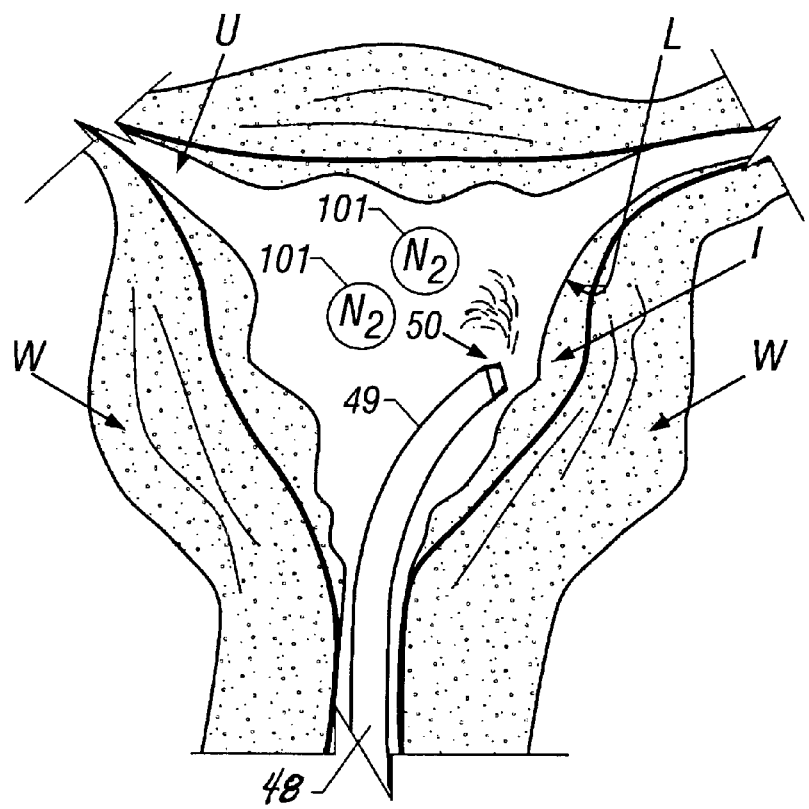
FIG. 3B is a first sequential view of the preferred embodiment of the method of assisted embryo implantation, which shows the survey of the endometrial lining for an implantation site.

Prior to any intrauterine activity, the embryo must be placed in the microcatheter 10 which will be used to both prepare the site for implantation and to transfer the embryo "E" into the site. Shown in FIG. 3A is an embryo "E" immersed in a culture medium "CM" placed near the front end 33 of the microcatheter 10. The culture medium "CM" serves the important role of maintaining the health and viability of the embryo "E" during the procedure. In this preferred embodiment the culture medium "CM" used is a "modified Human Tubal Fluid", manufactured by Irvine Scientific of Irvine, Calif. Considering the rapid pace of advancements in IVF, new and varied culture media will undoubtedly be developed or become available. Accordingly, the scope of this invention should not be limited to that culture media described herein, but rather to any suitable culture media which serves the function of maintaining embryo viability during the implantation procedure.

Prior to placing the embryo "E" into the microcatheter 10, a first quantity of culture medium "CM" is drawn into the microcatheter 10 and followed by a back measure of atmospheric air "A2". Next, the embryo "E", bathed in more culture medium "CM", is drawn into the microcatheter's front end 33 followed by a front measure of atmosphere air "A", thereby sandwiching the embryo "E" between a first and second measure of atmospheric air "A" and "A2". Once loaded with the embryo "E", the microcatheter 10 is ready for use in the implantation procedure. Each measure of atmospheric air should be about three to twenty microliters in volume.

To begin the preferred implantation procedure, the insertion section 42 of the hysteroscope 40 is guided into the uterus "U". During the insertion of the hysteroscope 40, $N_2$ gas 101 is fed into the uterus "U" pressurizing or insufflating the uterus "U" and thereby distending the uterine walls "W". Depending on the needs of the operator, and the uterus of the subject, the gas 101 may be automatically maintained at a constant pressure or the operator may vary the pressure. The distension of the uterine walls "W" enhances the hysteroscopic 40 visualization within the uterus "U".

Figure 3C:
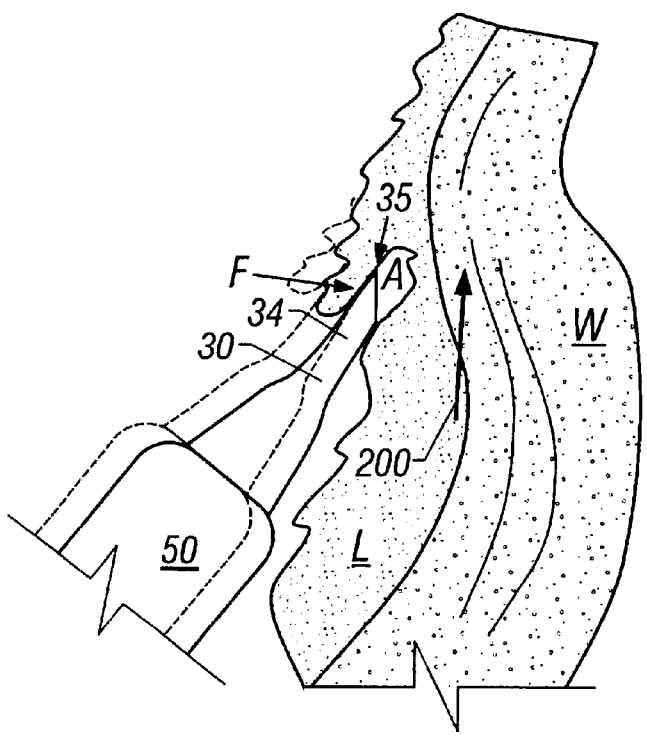
FIG. 3C is a second sequential view of the preferred embodiment of the method of assisted embryo implantation, which shows the formation of an embryo-receiving pocket at the selected implantation site.
Figure 3D:
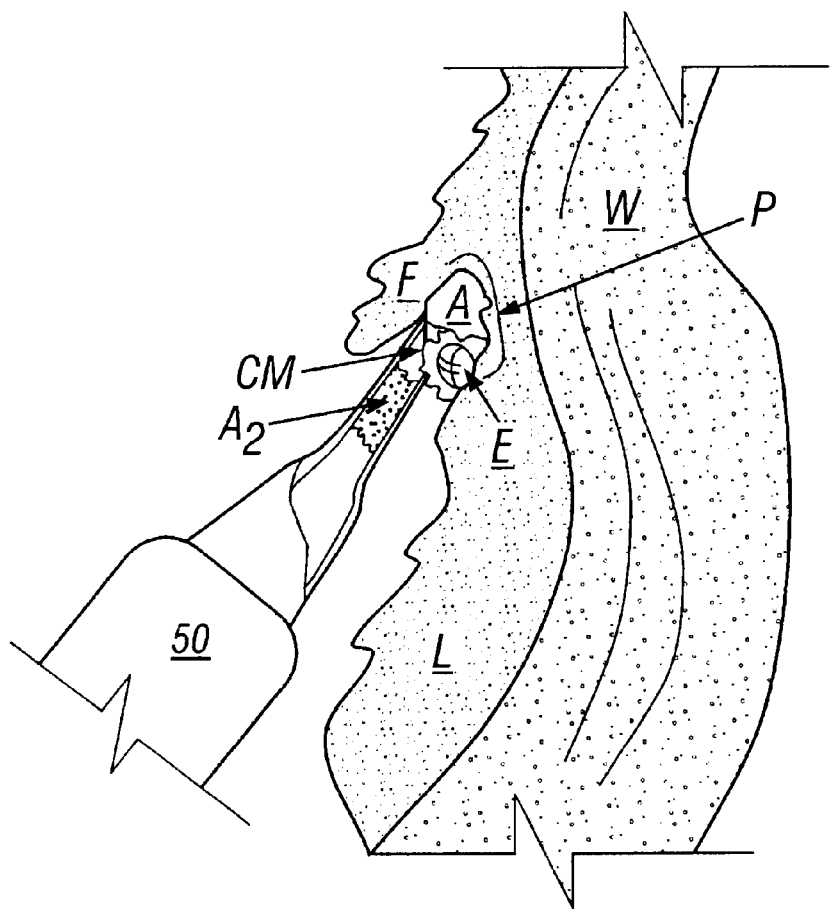
FIG. 3D is a third sequential view of the preferred embodiment of the method of assisted embryo implantation, which shows the implantation of the embryo within the pocket of FIG. 3B.
Figure 3E:
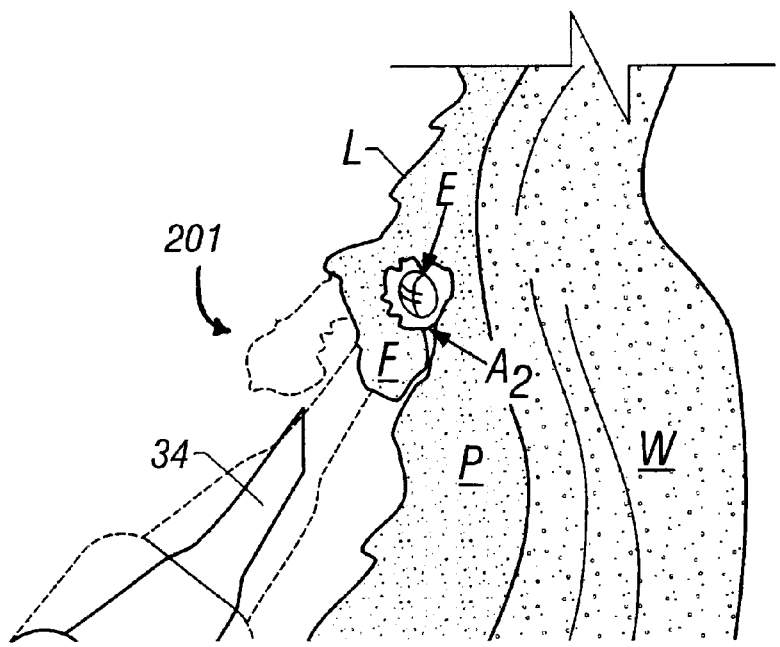
FIG. 3E is a fourth sequential view of the preferred embodiment of the method of assisted embryo implantation, which shows the closure of the embryoreceiving pocket over the embryo.

Once an embryo implantation site "I" is selected, the shaped end of the microcatheter 30 is inserted into the endometrial lining "L" (FIG. 3) and the angled tip 34 is moved generally along the path of arrow 200 making a small incision 2–5 millimeters deep in the endometrial lining "L" to form a small flap "F". The front measure of atmospheric air "A" is then released from the microcatheter and acts to lift up the small flap "F" of the endometrial lining "L". Shown in FIG. 3C is the embryo-receiving pocket "P" formed beneath the small flap "F". The actual implantation of the embryo "E" into the embryo-receiving pocket "P" (FIG. 3D) is performed with the same microcatheter 30 used to form the embryo-receiving pocket "P" and is accomplished by depressing the syringe's 20 plunger 21 to gently urges the embryo "E" and the back measure of atmospheric air "A2" out of the microcatheter 30 and into embryo-receiving pocket "P".

The back measure atmospheric air "A2" forms a cushion around the embryo "E" which helps to protect it when the microcatheter is removed (FIG. 3E) and the small flap "F" drops back into place over the embryo "E" along the line of arrow 201. To complete the procedure, the hysteroscope 40 is then gently removed from the subject and post-IVF precautions and protocols should be used. Another possible advantage of a successful implantation of the embryo "E" within the endometrial lining "L" is that the length of the post-IVF precautions may be reduced.

Dependent on the subject, the number of viable embryos available and the aperture, up to two embryos may be implanted into a single pocket "P". In the case of embryo implantations into multiple pockets, additional embryos, each bathed in culture medium, are sandwiched between a measure of atmospheric air within the microcatheters and implanted into separately formed pockets "P".

Certain presently preferred embodiments of apparatus and methods for practicing the invention have been described herein in some detail and some potential modifications and additions have been suggested. Other modifications, improvements and additions not described in this document may also be made without departing from the principles of the invention.

I claim:

1. A method of assisted embryo implantation comprising the steps of:
   a. selecting a site for implantation within the endometrial lining of the subject's uterus;
   b. placing one or more embryos bathed in a fluid culture medium, proceeded by a front measure of atmospheric air, near the open end of a microcatheter;
   c. inserting said open end of said microcatheter into the endometrial lining at the embryo implantation site, and using said open end to open a small flap of the endometrial lining, thereby creating a pocket to receive one or more embryos;
   d. using said microcatheter to transfer said front measure of atmospheric air under the small flap thereby causing the small flap to raise;
   e. using said microcatheter to deposit the embryo(s) and culture medium under the raised small flap and into the pocket; and,
   f. withdrawing said microcatheter thereby allowing the small flap to close over the pocket.

2. The method of claim 1 wherein visual guidance through an endoscopic device is used to direct said microcatheter during steps "c", "d" and "e".

3. The method of claim 1 wherein during step "c" a pressurized gas is added to the uterus, thereby causing the uterine walls to distend.

4. The method of claim 1 wherein:
   a. step "b" further comprises placing a back measure of atmospheric air in the microcatheter behind the embryo (s); and,
   b. step "e" further comprises adding said back measure of atmospheric air into the pocket, thereby providing a cushion surrounding the embryo(s).

5. The method of claim 1 wherein said open end is an angled tip.

6. The method of claim 5 wherein said angled tip is beveled forming a thin outer edge around at least a portion of its periphery.

7. The method of claim 5 wherein at least a portion of said angled tip is tapered towards its periphery forming an edge capable of cutting into the endometrial lining.

8. The method of claim 1 wherein the one or more embryos are between 4–6 days old.

9. The method of claim 3 wherein the gas is selected from the group consisting of inert "noble" gases.

10. The method of claim 3 wherein the inert noble gas is $N_2$.

11. The method of claim 3 wherein the gas is maintained at a selected pressure.

12. A method of assisted embryo implantation comprising the steps of:
   a. placing at least one 4 to 6 day old embryo, bathed in a solution of culture medium, into a flexible microcatheter having a generally tubular body with an angled tip;
   b. placing a front measure of atmospheric air into said microcatheter in front of the embryo(s);
   c. inserting the flexible end of an endoscopic visualization device, with one or more operative channels, into the subject's uterus and visually inspecting the endometrial lining for an embryo implantation site;
   d. during step "c", causing the subject's uterine walls to distend by adding a gas into the uterus through one of said operative channels and selectively maintaining some degree of the distension throughout the implantation;
   e. inserting said microcatheter through one of said operative channels and extending said angled tip into the endometrial lining at the embryo implantation site;
   f. using said angled tip to open a small flap of the endometrial lining and thereby form a pocket, about two millimeters to about six millimeters in depth, to receive the embryo(s);
   g. using said microcatheter to transfer said front measure of atmospheric air under the small flap thereby raising the small flap;
   h. using said microcatheter to place the embryo(s) and culture medium under the raised small flap and into the pocket; and,
   i. withdrawing said microcatheter thereby allowing the small flap to cover the pocket.

13. The method of claim 12 wherein:
   a. step "a" further comprises placing a back measure of atmospheric air into said microcatheter behind the embryo(s); and
   b. step "h" further comprises depositing said back measure of atmospheric air into the pocket, immediately following the placement of the embryo(s) within the pocket, thereby providing a cushion surrounding the embryo(s).

14. The method of claim 13 wherein the amount of the back measure of atmospheric air which is deposited in the pocket is approximately 10–15 microliters.

15. The method of claim 12 wherein said generally tubular body tapers approximately 1.5 centimeters prior to said angled tip to a diameter of approximately 0.8 millimeters.

16. The method of claim 12 wherein said angled tip is beveled around at least a portion of its periphery forming a thin outer edge sufficiently sharp to cut into the endometrial lining.

17. The method of claim 12 wherein the gas is an inert "noble" gas.

18. The method of claim 17 wherein the inert "noble" gas is $N_2$.

19. The method of claim 12 wherein the endoscopic device is a hysteroscope.

20. The method of claim 12 wherein the fluid medium is "modified Human Tubal Fluid".

21. A method of assisted embryo implantation comprising the steps of:
   a. placing at least one 3 to 6 day old embryo surrounded in modified Human Tubal Fluid into the generally tubular body of a flexible microcatheter which tapers to form a smaller diameter tip with an angled leading edge;
   b. placing a front measure of atmospheric air in said microcatheter in front of the embryo(s);
   c. placing a back measure of at least 10 microliters of atmospheric air in said microcatheter behind the embryo(s);
   d. inserting the flexible end of a hysteroscopic visualization device, with an single operative channel, into the subject's uterus;
   e. distending the subject's uterus by adding pressured $N_2$ gas through the operative channel and maintaining some degree of distension during the implantation;
   f. using the hysteroscope to visually inspect the endometrial lining of the distended uterus to select an embryo implantation site;
   g. inserting said microcatheter through said operative channel and extending said angular leading edge into the endometrial lining at the embryo implantation site;
   h. using said angled leading edge to cut open a small flap of the endometrial lining and thereby form a pocket, about three millimeters to about five millimeters in depth, to receive the embryo(s);
   i. using said microcatheter to transfer said front measure of atmospheric air under the small flap thereby raising the small flap;
   j. using said microcatheter to deposit the embryo(s) and modified Human Tubal Fluid under the raised small flap and into the pocket;
   k. using said microcatheter to deposit 5–10 microliters of said back measure of atmospheric air under the raised small flap; and
   l. withdrawing said microcatheter thereby allowing the small flap to cover the pocket.

* * * * *